(12) United States Patent
Suddaby et al.

(10) Patent No.: US 9,566,163 B2
(45) Date of Patent: Feb. 14, 2017

(54) EXPANDABLE SPINAL IMPLANT

(71) Applicant: K2M, Inc., Leesburg, VA (US)

(72) Inventors: Loubert Suddaby, Orchard Park, NY (US); Larry McClintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 322 days.

(21) Appl. No.: 14/464,892

(22) Filed: Aug. 21, 2014

(65) Prior Publication Data

US 2015/0057755 A1    Feb. 26, 2015

Related U.S. Application Data

(60) Provisional application No. 61/868,499, filed on Aug. 21, 2013.

(51) Int. Cl.
*A61F 2/44* (2006.01)
*A61F 2/46* (2006.01)
*A61F 2/30* (2006.01)

(52) U.S. Cl.
CPC ............ *A61F 2/4425* (2013.01); *A61F 2/44* (2013.01); *A61F 2/442* (2013.01); *A61F 2/447* (2013.01); *A61F 2/4455* (2013.01); *A61F 2/46* (2013.01); *A61F 2/4603* (2013.01); *A61F 2/4611* (2013.01); *A61F 2002/3054* (2013.01); *A61F 2002/30266* (2013.01); *A61F 2002/30281* (2013.01); *A61F 2002/30484* (2013.01); *A61F 2002/30522* (2013.01); *A61F 2002/30538* (2013.01); *A61F 2002/30556* (2013.01); *A61F 2002/30566* (2013.01); *A61F 2002/30568* (2013.01); *A61F 2002/30594* (2013.01); *A61F 2002/30626* (2013.01); *A61F 2002/30629* (2013.01); *A61F 2002/30828* (2013.01); *A61F 2002/30831* (2013.01); *A61F 2002/448* (2013.01);
(Continued)

(58) Field of Classification Search
CPC ............ A61F 2002/30522; A61F 2002/30538; A61F 2002/3054; A61F 2/44; A61F 2/442; A61F 2/4425; A61F 2/4455; A61F 2/447; A61F 2002/448; A61F 2/46; A61F 2/4603; A61F 2/4611; A61F 2250/0004; A61F 2250/0006
See application file for complete search history.

(56) References Cited

U.S. PATENT DOCUMENTS

5,554,191 A    9/1996  Lahille et al.
6,159,244 A   12/2000  Suddaby
(Continued)

*Primary Examiner* — Larry E Waggle, Jr.
(74) *Attorney, Agent, or Firm* — Carter, DeLuca, Farrell & Schmidt, LLP (57) ABSTRACT

An expandable spinal implant configured for positioning within the intervertebral space between adjacent vertebral bodies is disclosed. The spinal implant includes a first body, a second body, a ratchet, and a locking mechanism. The first and second bodies are pivotably affixed to each other on respective first ends thereof and are capable of movement relative to each other in a medial-lateral direction with respect to the adjacent vertebral bodies. The ratchet is pivotably supported within a slot defined in the first body and is capable of engaging the second body thereby permitting movement of the first and second body relative to each other in a first direction, but not in a second direction that is different than the first direction. A method of performing spinal surgery is also disclosed.

18 Claims, 5 Drawing Sheets

(52) U.S. Cl.
CPC .............. *A61F 2002/4475* (2013.01); *A61F 2250/0004* (2013.01); *A61F 2250/0006* (2013.01); *A61F 2310/00023* (2013.01); *A61F 2310/00029* (2013.01)

(56) References Cited

U.S. PATENT DOCUMENTS

| | | |
|---|---|---|
| 6,176,882 B1 | 1/2001 | Biedermann et al. |
| 6,190,414 B1 | 2/2001 | Young et al. |
| 6,193,757 B1 * | 2/2001 | Foley .................. A61F 2/4455 623/17.16 |
| 6,443,989 B1 | 9/2002 | Jackson |
| 6,454,807 B1 | 9/2002 | Jackson |
| 6,576,016 B1 | 6/2003 | Hochshuler et al. |
| 6,685,742 B1 | 2/2004 | Jackson |
| 6,808,537 B2 | 10/2004 | Michelson |
| 6,814,756 B1 | 11/2004 | Michelson |
| 7,044,971 B2 | 5/2006 | Suddaby |
| 7,118,579 B2 | 10/2006 | Michelson |
| 7,217,291 B2 | 5/2007 | Zucherman et al. |
| 7,217,293 B2 | 5/2007 | Branch, Jr. |
| 7,678,148 B2 | 3/2010 | Peterman |
| 7,799,081 B2 | 9/2010 | McKinley |
| 8,398,713 B2 | 3/2013 | Weiman |
| 8,496,706 B2 | 7/2013 | Ragab et al. |
| 8,518,114 B2 | 8/2013 | Marik |
| 8,628,578 B2 | 1/2014 | Miller et al. |
| 8,679,183 B2 | 3/2014 | Glerum et al. |
| 8,795,366 B2 | 8/2014 | Varela |
| 2004/0087947 A1 | 5/2004 | Lim et al. |
| 2006/0122701 A1 | 6/2006 | Kiester |

* cited by examiner

EXPANDABLE SPINAL IMPLANT

CROSS-REFERENCE TO RELATED APPLICATION

This application claims priority to, and the benefit of, U.S. Provisional Patent Application Ser. No. 61/868,499, filed on Aug. 21, 2013, the entire contents of which are incorporated by reference herein.

TECHNICAL FIELD

The present disclosure relates generally to devices and methods for treating spinal conditions, and in particular, to expandable spinal implants configured for positioning within an intervertebral space.

BACKGROUND

The human spine includes thirty-three vertebrae. The vertebrae interlock with one another to form a spinal column. Each vertebra has a cylindrical bony body (vertebral body), two pedicles extending from the vertebral body, a lamina extending from the pedicles, two wing-like projections extending from the pedicles, a spinous process extending from the lamina, a pars interarticularis, two superior facets extending from the pedicles, and two inferior facets extending from the lamina. The vertebrae are separated and cushioned by thin pads of tough, resilient fiber known as intervertebral discs. Intervertebral discs provide flexibility to the spine and act as shock absorbers during activity. A small opening (foramen) located between each vertebra allows passage of nerves. When the vertebrae are properly aligned, the nerves pass through without a problem. However, when the vertebrae are misaligned or a constriction is formed in the spinal canal, the nerves get compressed and may cause back pain, leg pain, or other neurological disorders.

Disorders of the spine that may cause misalignment of the vertebrae or constriction of the spinal canal include spinal injuries, infections, tumor formation, herniation of the intervertebral discs (i.e., slippage or protrusion), arthritic disorders, and scoliosis. In these pathologic circumstances, surgery may be tried to either decompress the neural elements and/or fuse adjacent vertebral segments. Decompression may involve laminectomy, discectomy, or corpectomy. Laminectomy involves the removal of part of the lamina, i.e., the bony roof of the spinal canal. Discectomy involves removal of the intervertebral discs. Corpectomy involves removal of the vertebral body as well as the adjacent intervertebral discs.

The time-honored method of addressing the issues of neural irritation and instability resulting from severe disc damage have largely focused on removal of the damaged disc and fusing the adjacent vertebral elements together. Removal of the disc relieves the mechanical and chemical irritation of neural elements, while osseous union (bone knitting) solves the problem of instability.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, many spinal surgeons have found that interbody fusion using bone alone has an unacceptably high rate of bone graft migration, expulsion, or nonunion due to structural failures of the bone or residual degrees of motion that retard or prohibit bony union. Therefore, intervertebral prostheses in various forms have been used to provide immediate stability and to protect and preserve an environment that fosters growth of grafted bone such that a structurally significant bony fusion can occur.

Many intervertebral implants have one or more fixed dimensions that may create challenges and/or lead to compromises when selecting a suitable implant for a surgical procedure.

Therefore, a need exists for an expandable spinal implant that can be inserted in a collapsed state in order to prevent over retraction of the anatomy, a reduction in surgical morbidity, and/or substandard implant sizing. Once the expandable spinal implant is in place, it can then be expanded to fill the anatomical space appropriately.

SUMMARY

In accordance with the present disclosure, a spinal implant including a first body, a second body, and a ratchet mechanism is provided. The first and second bodies are pivotably affixed to each other at respective first ends thereof and are capable of movement relative to each other. The first and second bodies are dimensioned to be installed between two vertebral bodies and the outer surfaces of each of the first and second bodies are adapted to engage the vertebral bodies. The movement of the first and second bodies is in a medial-lateral direction relative to the two vertebral bodies. A ratchet mechanism is pivotably supported within a slot defined in a recess of the first body. The ratchet mechanism is capable of engaging a portion of the second body thereby permitting movement of the first and second bodies relative to each other in a first direction, and inhibiting movement in a second direction different than the first direction.

In aspects, outer surfaces of the first body and the second body include ridges adapted to engage the first and second vertebral bodies.

In aspects, at least one biasing element is disposed within a counterbore defined in the recess of the first body. The at least one biasing element is adapted to bias the ratchet mechanism into engagement with the second body.

In aspects, the ratchet mechanism includes a first plurality of teeth disposed thereon.

In aspects, the second body includes a second plurality of teeth disposed on an interior surface thereon opposite the ratchet mechanism. The second plurality of teeth is configured to engage the first plurality of teeth of the ratchet mechanism.

In aspects, the first and second pluralities of teeth are oriented such that the first and second pluralities of teeth are slidably engaged in a first direction, and are prohibited from movement relative each other in a second direction different from the first direction, thereby defining a predetermined size of the spinal implant.

In aspects, the spinal implant further includes a locking mechanism disposed within an orifice defined in a side surface of the ratchet mechanism and a keyhole defined in an end face of the second body.

In aspects, the locking mechanism includes first and second ends, wherein the second end is capable of advancing axially within the keyhole in a first, unlocked position. The second end is also capable of locking the ratchet mechanism into a selected position when in a second, locked, position.

In aspects, the spinal implant is capable of being inserted between two vertebral bodies using a tool.

In aspects, the first and second bodies are capable of being manipulated relative to each other using a tool.

In aspects, the first end of the locking mechanism is attachable to a tool.

A method of performing surgery provided in accordance with the present disclosure includes providing a spinal implant comprising a first body, a second body, and a ratchet mechanism. The first and second bodies are pivotably affixed to each other at respective first ends thereof and are capable of movement relative to each other. The first and second bodies are dimensioned to be installed between two vertebral bodies and the outer surfaces of each of the first and second bodies are adapted to engage the vertebral bodies. The movement of the first and second bodies may be in a medial-lateral direction relative to the two vertebral bodies. A ratchet mechanism is pivotably supported within a slot defined in a recess of the first body. The ratchet mechanism is capable of engaging a portion of the second body thereby permitting movement of the first and second bodies relative to each other in a first direction, and inhibiting movement in a second direction different than the first direction. The method further includes positioning the first body and the second body in a first, approximated position relative each other, preparing an intervertebral space between first and second vertebral bodies to receive the spinal implant, inserting the spinal implant into the prepared intervertebral space, articulating the first body and the second body relative to each other to obtain a desired medial-lateral footprint within the intervertebral space, and locking the ratchet mechanism to define a predetermined size of the spinal implant.

In aspects, inserting the spinal implant includes first securing the spinal implant to an insertion device.

In aspects, locking the ratchet mechanism includes rotating a locking mechanism disposed within an orifice defined within a side surface of the ratchet mechanism and a keyhole defined in an end face of the second body. The locking mechanism includes first and second ends, and is capable of advancing axially within the keyhole. Rotating the tool causes the locking mechanism to rotate to a locked position.

In aspects, positioning the first body and second body in a first, approximated, position includes engaging a first plurality of teeth disposed on a surface of the ratchet mechanism with a second plurality of teeth disposed on an opposing surface of other one of the first body and second body, thereby permitting articulation of the first body relative to the second body in a first direction, but not in a second direction.

In aspects, inserting the spinal implant includes attaching an insertion instrument to the spinal implant.

In aspects, articulating the first body relative to the second body includes manipulating an insertion instrument, thereby causing the first body and the second body to articulate relative to each other.

In aspects, locking the ratchet mechanism further includes attaching a tool to a first end of the locking mechanism.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF THE EMBODIMENTS

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Figure 1:
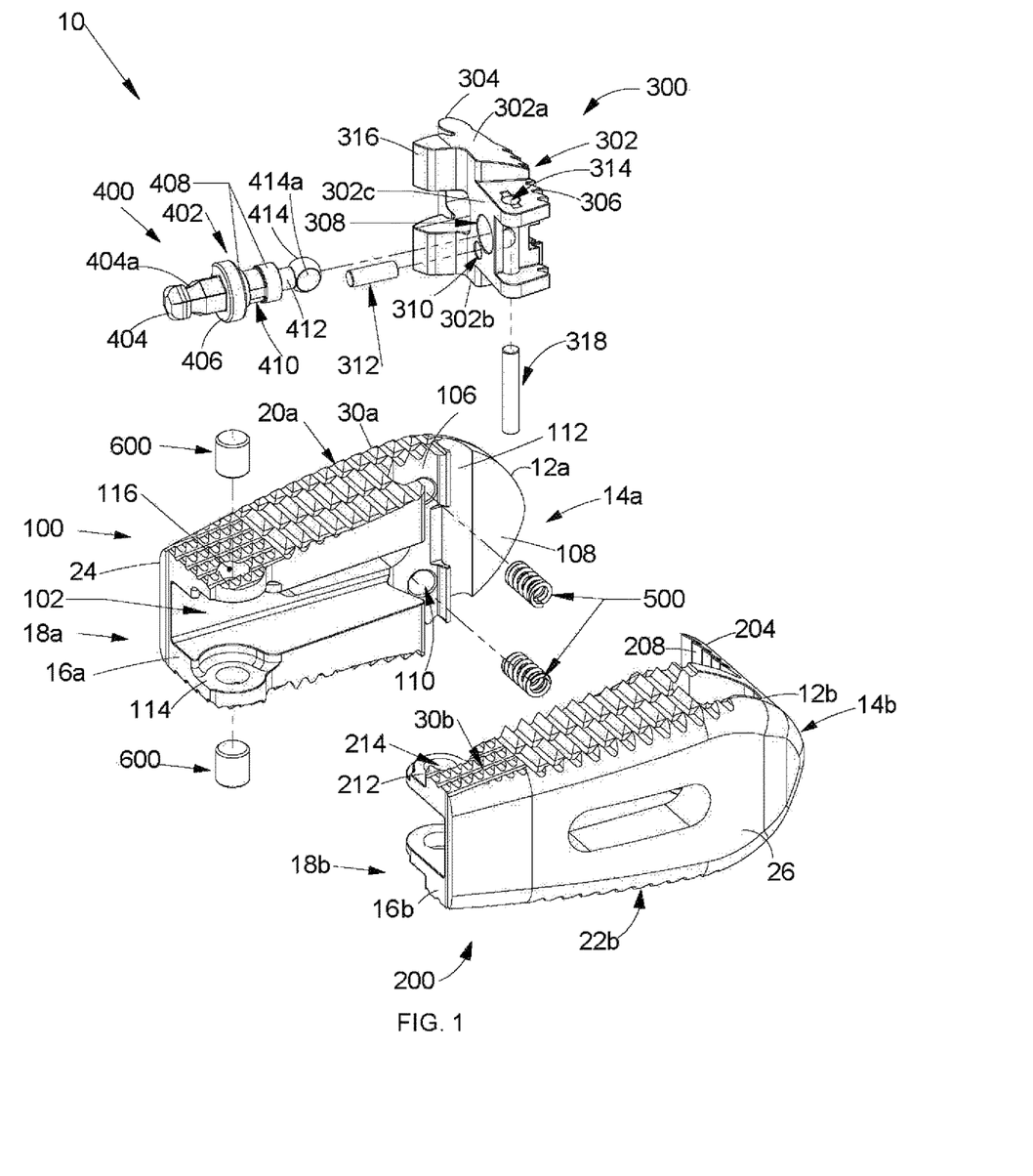
FIG. 1 is an exploded view, with parts separated, of an expandable spinal implant provided in accordance with the present disclosure.

Referring now to the drawings, FIG. 1 illustrates an embodiment of expandable spinal implant 10 provided in accordance with the present disclosure. Expandable spinal implant 10 includes a first body 100, a second body 200, a ratchet mechanism 300, a locking mechanism 400, biasing elements 500, and hinge pins 600. First and second bodies 100, 200 cooperate to define a two part expandable spinal implant configured for positioning between adjacent vertebral bodies. Ratchet mechanism 300 and locking mechanism 400 cooperate to provide a locking mechanism to lock first and second bodies 100, 200 in an expanded position relative to each other, thereby expanding the medial-lateral footprint of expandable spinal implant 10. Each of these components along with the assembly and insertion of expandable spinal implant 10 into the intervertebral space, as well as the expansion/contraction of expandable spinal implant 10 within the intervertebral space will be described in turn hereinbelow.

The various components of expandable spinal implant 10, or portions thereof, may be formed from various similar or different materials, depending on a particular purpose. In particular, first and second bodies 100, 200 may be formed from a metallic material (e.g., titanium, titanium alloy, or cobalt chrome (CoCr)) or a non-metallic material (e.g., polymeric materials such as polyetheretherketone (PEEK), non-absorbable polymers, nylon absorbable polymers such as polyglycolides, polylactides, polycaprolactone, etc., or organic materials such as bone) and ceramic materials. Ratchet mechanism 300, locking mechanism 400, biasing elements 500, and hinge pins 600 may be formed from titanium, titanium alloy, CoCr or other suitable metal or polymeric material compatible with first and second bodies 100, 200.

Figure 2:
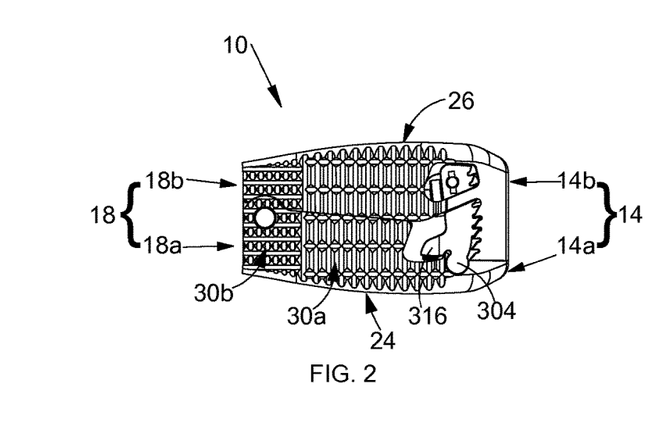
FIG. 2 is a top view of the expandable spinal implant of FIG. 1, shown in a closed position.
Figure 3:
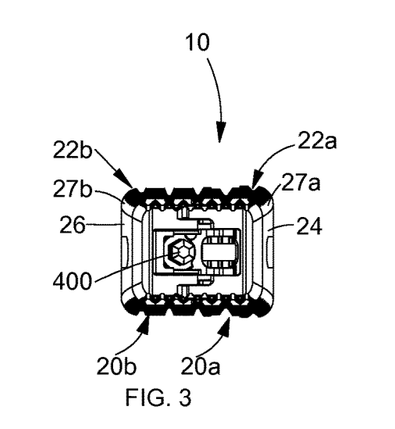
FIG. 3 is an end view of the expandable spinal implant of FIG. 1, shown in the closed position.
Figure 4:
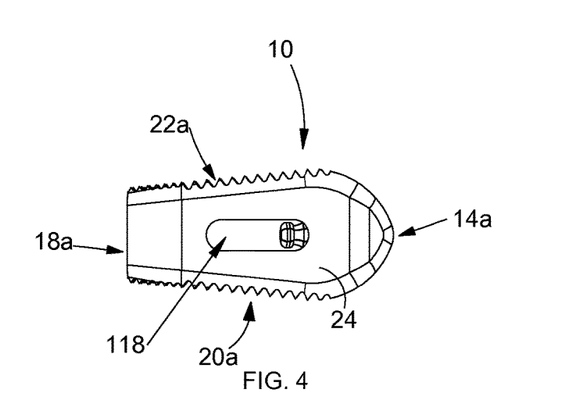
FIG. 4 is a side view of the expandable spinal implant of FIG. 1, shown in the closed position.
Figure 8:
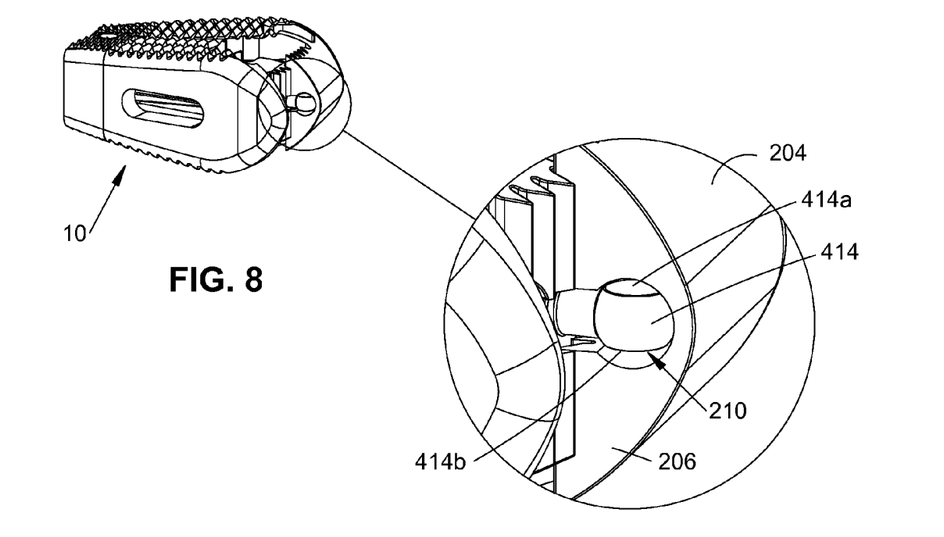
FIG. 8 is an enlarged view of a locking mechanism of the expandable spinal implant of FIG. 1, shown in an unlocked position.

With reference to FIGS. 1, 2, and 8, expandable spinal implant 10 is illustrated. Expandable spinal implant 10 is formed by first and second bodies 100, 200, which are operable to be positioned in an expanded state (FIG. 5), or a closed state (FIG. 2). Expandable spinal implant 10 includes substantially contoured first end surfaces 12a, 12b at a distal or leading end 14a, 14b of first and second bodies 100, 200, respectively, and second end surfaces 16a, 16b opposite thereto at a proximal or trailing end 18a, 18b, of first and second bodies 100, 200, respectively. Expandable spinal implant 10 extends between the first and second end surfaces 12a, 12b and 16a, 16b to define respective top and bottom surfaces 20a, 20b, 22a, and 22b, as well as opposed side surfaces 24, 26. As illustrated in FIG. 3, the top and bottom surfaces 20a, 20b and 22a, 22b, engage side surfaces 24, 26, respectively, to provide a substantially rectangular cross-sectional profile, with rounded corners 27a, 27b. As best illustrated in FIGS. 2 and 4, first end surfaces 12a, 12b form a substantially atraumatic blunt nose profile, and second end surfaces 16a, 16b form a substantially flat or planar profile. For a more detailed discussion of the profile of expandable spinal implant 10, reference may be made to U.S. Pat. No. 8,801,791, filed on Sep. 27, 2007, entitled "Spinal Interbody Spacer," the entirety of which is incorporated herein by reference.

Referring now to FIGS. 3 and 4, top surfaces 20a, 20b are generally shown as being angled with respect to bottom surfaces 22a, 22b in a direction from leading end 14 to trailing end 18 thereby defining a lordotic taper capable of effectuating lordosis of the spine when expandable spinal implant 10 is advanced within the intervertebral space. Although generally shown as being angled with respect to each other such that the trailing end 18 has a height that is less than a height of the leading end 14, it is contemplated that top surfaces 20a, 20b and bottom surfaces 22a, 22b may be angled with respect to each other such that leading end 14 has a height that is less than a height of the trailing end 18. It is also contemplated that top surface 20 may be parallel to bottom surface 22.

As illustrated in FIGS. 1 and 4, top and bottom surfaces 20a, 20b, 22a, and 22b define a first plurality of ridges 30a and a second plurality of ridges 30b arranged thereon. The first plurality of ridges 30a are disposed proximate to leading ends 14a, 14b and the second plurality of ridges 30b are disposed proximate to trailing ends 18a, 18b, each of which are configured to frictionally engage an adjacent surface of a vertebral body VB (i.e., a vertebral endplate) to prevent expandable spinal implant 10 from backing out of the intervertebral space since the ridges 30a and 30b will bite into the adjacent vertebral plate. First and second pluralities of ridges 30a, 30b include distinct profiles (i.e., first plurality of ridges 30a may have an elongate triangular profile, while second plurality of ridges 30b may have a pyramidal profile); however, it is contemplated that first and second pluralities of ridges 30a, 30b may have similar profiles. For a detailed discussion of the construction of exemplary ridges, reference may be made to U.S. Pat. No. 8,801,791, filed on Sep. 27, 2007, entitled "Spinal Interbody Spacer," the entirety of which is incorporated herein by reference.

Figure 5:
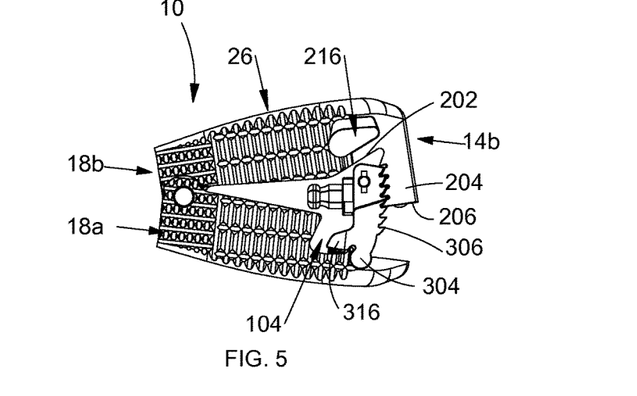
FIG. 5 is a top view of the expandable spinal implant of FIG. 1, shown in an expanded position.

Referring now to FIGS. 1 and 5, an illustration of first body 100 is shown. Channel 102 is defined through first and second end surfaces 12a, 16a and is substantially parallel to side surface 24; however, it is contemplated that channel 102 may approximate side surface 24 in a direction from trailing end 18a towards leading end 14a and vice versa. Although generally shown as having a substantially U-shaped configuration, it is contemplated that channel 102 may have other suitable cross sections, such as v-shaped, circular, or oval.

Relief 104 (FIG. 5) is illustrated as being defined through top and bottom surfaces 20a, 22a adjacent to leading end 14a, and defines faces 106, 108, extending substantially perpendicular to top and bottom surfaces 20a, 22a. Counterbores 110 are defined in face 106 and are configured and/or dimensioned to receive biasing elements 500, such that biasing elements 500 bias ratchet mechanism 300 into engagement with teeth 208 of second body 200, thereby permitting motion in a first direction, and inhibiting motion in a second, opposite direction. Pivot slot 112 is defined in face 108 and is open at the top and bottom surfaces 20a, 22a. Pivot slot 112 includes a circular cross section with less than half of the circumference open such that pivot 304 of ratchet mechanism 300 is rotatably secured therein.

Counterbores 114 are defined within each of the upper and lower inner surfaces of channel 102, adjacent to trailing end 18a and side surface 24. Through-holes 116 are defined through upper surface 20a and lower surface 22a and are concentric with counterbore 114. Through-holes 116 are configured to frictionally retain hinge pins 600 therein.

With reference to FIG. 4, slot 118 is defined through side surface 24 and includes an elongate shape complimentary to that of side surface 24 of first body 100; however, it is contemplated that slot 118 may include other suitable shapes such as circular, rectangular, or the like. It is further contemplated that slot 118 may include a plurality of individual apertures.

Referring back to FIGS. 1 and 5, an illustration of second body 200 is shown generally as having a shape complimentary to that of first body 100 (i.e., mirrored) and thus, in the interest of brevity, only the differences between first body 100 and second body 200 will be detailed herein. Extension 204 extends from inner face 202 (adjacent to leading end 14b) and terminates in end face 206 (FIG. 5). Teeth 208 are disposed on an opposing face to that of first end surface 12b and are configured to engage teeth 306 of ratchet mechanism 300 such that when in an unlocked position, first body 100 and second body 200 may pivot or rotate relative to each other in a first direction causing expandable spinal implant 10 to expand, but not in a second direction allowing expandable spinal implant 10 to contract (i.e., a direction causing first and second bodies 100, 200 to approximate each other). Teeth 208 are generally shown as being arranged in an arcuate profile (when viewed looking towards top surface 20b); however, it is contemplated that teeth 208 may have other suitable profiles, such as planar. Keyhole 210 (FIG. 8) is defined through end face 206 and includes a circular cross section and an intersecting rectangular cross section such that keyhole 210 is defined through teeth 208. Keyhole 210 is configured to receive leading end 414 of locking mechanism 400.

Counterbores 212 are disposed within top and bottom surfaces 20b, 22b of second body 200 adjacent to trailing end 18b and are complimentary to counterbores 114 of first body 100 such that counterbores 114 and 212 interlock (i.e., counterbores 212 pass within counterbores 114). Through-bore 214 is defined through top and bottom surfaces 20b, 22b and is concentric with counterbores 212. Through-bore 214 is configured and/or dimensioned to rotatably receive hinge pins 600 therein, such that hinge pins may be pressed into through-hole 116 (held in frictional engagement) and pass through through-bore 214 such that first and second bodies 100, 200 are pivotably/rotatably retained thereabout. Hinge pins 600 may be any suitable pin, such as a dowel pin, a roll pin, or the like.

Aperture 216 (FIG. 5) is defined through top and bottom surfaces 20b, 22b at a location where first end surface 14b and side surface 26 intersect.

Continuing with FIGS. 1 and 5, an illustration of ratchet mechanism 300 is shown. Ratchet mechanism 300 includes first and second ends defining elongate body 302 therebetween. Pivot 304 is disposed on the first end of elongate body 302 and includes a substantially circular cross section extending from upper surface 302a to lower surface 302b. Pivot 304 is configured and/or adapted to be received within pivot slot 112 of first body 100 such that ratchet mechanism 300 is pivotably secured therein. Boss 316 extends from a side surface 302c adjacent to pivot 304 and is configured to engage biasing elements 500, thereby biasing ratchet mechanism 300 into engagement with teeth 208 of second body 200, thereby permitting motion in a first direction, and inhibiting motion in a second, opposite direction. Teeth 306 are disposed on a second, opposing side surface and are configured to engage teeth 208 of second body 200. Teeth 306 are arranged in a profile complimentary to that of teeth 208 of second body 200, such as arcuate; however, it is contemplated that teeth 306 may be arranged in any suitable profile that is complimentary to that of the profile of teeth 208. Orifice 308 is defined through side surface 302c and teeth 306, and is configured to receive locking mechanism 400 such that locking mechanism 400 is rotatably secured therein. Bore 310 is defined through side surface 302c proximate to orifice 308 and is configured to frictionally retain limiting pin 312 therein. Limiting pin 312 may be any suitable pin, such as a dowel, a roll pin, or the like, and is disposed within bore 310, thereby limiting the rotational motion of locking mechanism 400. Retaining bore 314 is defined through upper surface 302a and intersects a portion of orifice 308, such that when retaining pin 318 is frictionally retained therein, locking mechanism 400 is prevented from advancing axially in orifice 308. Retaining pin 318 may be any suitable pin, such as a dowel, a roll pin, or the like.

Figure 6:
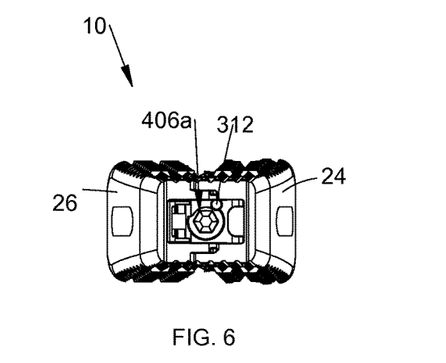
FIG. 6 is an end view of the expandable spinal implant of FIG. 1, shown in an expanded position.
Figure 7:
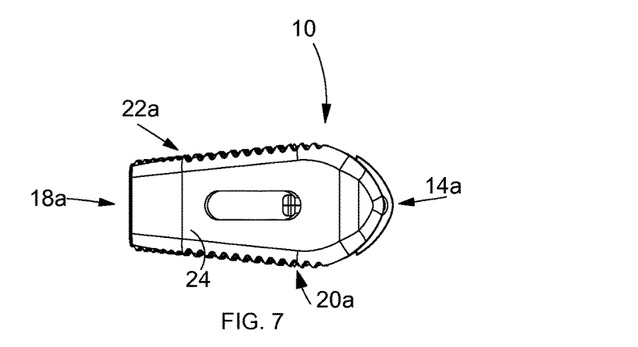
FIG. 7 is a side view of the expandable spinal implant of FIG. 1, shown in an expanded position.
Figure 9:
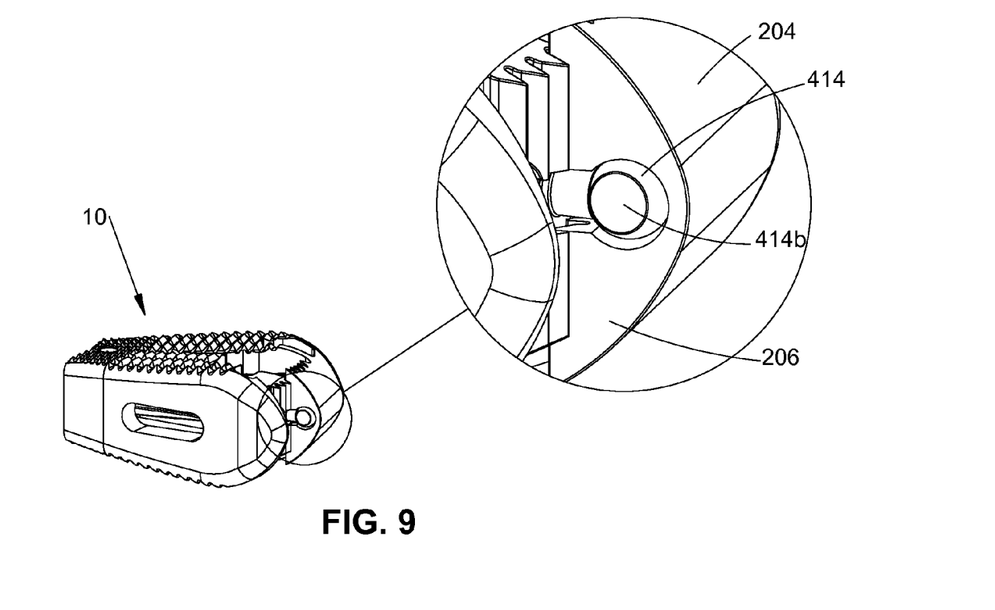
FIG. 9 is an enlarged view of the locking mechanism of FIG. 8, shown in a locked position.

An illustration of locking mechanism 400 is shown in FIGS. 1, 8 and 9. Locking mechanism 400 includes an elongate body 402 including first and second ends. The first end of elongate body 402 includes a hexagonal cross section 404. Hexagonal cross section 404 includes annular groove 404a defined therein capable of engaging a suitable tool (not shown). Hexagonal cross section 404 transitions to a flange 406 having a circular cross section extending in a direction towards the second end. Flange 406 includes a larger diameter than that of hexagonal cross section 404 and is configured to abut side surface 302c of ratchet mechanism 300, thereby inhibiting locking mechanism from passing entirely through orifice 308. Flange 406 includes a notch 406a (FIG. 6). Notch 406a is configured to act as a limiter to enable locking mechanism 400 to rotate from a first, unlocked position, to a second, locked position by engaging limiting pin 312. Flange 406 transitions to first shank portion 408 having a circular cross section and a diameter less than that of flange 406 and is configured and/or dimensioned to be received within orifice 308 such that locking mechanism is rotatably supported therein. Recess 410 is disposed within first shank portion 408 and includes a circular cross section having a diameter less than that of first shank portion 408. Recess 410 is configured and/or dimensioned to receive a portion of retaining pin 312 when locking mechanism 400 is fully advanced within orifice 308, thereby inhibiting locking mechanism 400 from translating axially within orifice 308. First shank portion 408 transitions to second shank portion 412 having a circular cross section and a diameter less than that of first shank section 408 such that second shank portion 412 may be advanced within keyhole 210. Second shank portion 412 transitions to leading end 414 having a spherical cross section having a diameter complimentary to that of the circular cross section portion of keyhole 210. Leading end 414 includes opposing planar sides 414a, 414b disposed thereon. Opposing planar sides 414a, 414b reduce the diameter of leading end 414 to that of second shank portion 412 such that leading end 414 and second shank portion 412 may be advanced within keyhole 210 when locking mechanism is in an unlocked position (i.e., opposing planar sides 414a, 414b are parallel to upper surface 302a of ratchet mechanism 300), locking mechanism may advance axially within keyhole 210 as teeth 306 and teeth 208 slide past each other as first body 100 and second body 200 rotate in a first direction allowing expandable spinal implant 10 to expand (FIG. 8). Rotation of locking mechanism 400 may be effectuated using any suitable tool capable of transmitting rotational motion to locking mechanism 400. Rotation of locking mechanism 400 to a second, locked position orients opposing planar sides 414a, 414b normal to upper surface 302a of ratchet mechanism 300 (FIG. 9) such that the diameter of leading end 414 abuts the interior of keyhole 210 thereby prohibiting axial translation of locking mechanism 300 within keyhole 210. By rotating locking mechanism 400 to the locked position, teeth 208, 306 remain engaged with one another thereby fixing a size of expandable spinal implant 10. In other words, expandable spinal implant 10 is prohibited from expanding or contracting with locking mechanism 400 in the locked position. It is contemplated that the tool, when advanced over hexagonal cross section 404 and retained within annular groove 404a, may be used to retract ratchet mechanism 300 such that teeth 208, 306 become disengaged, thereby allowing expandable spinal implant 10 to rotate in the second direction and contract.

Figure 10:
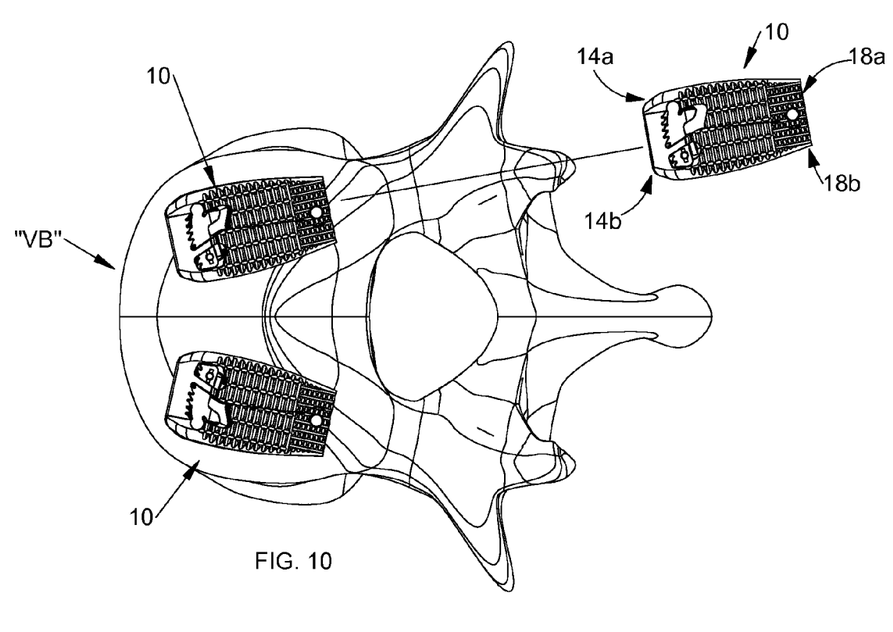
FIG. 10 is a plan view of an intervertebral space shown with two expandable spinal implants of FIG. 1 in a closed position.
Figure 11:
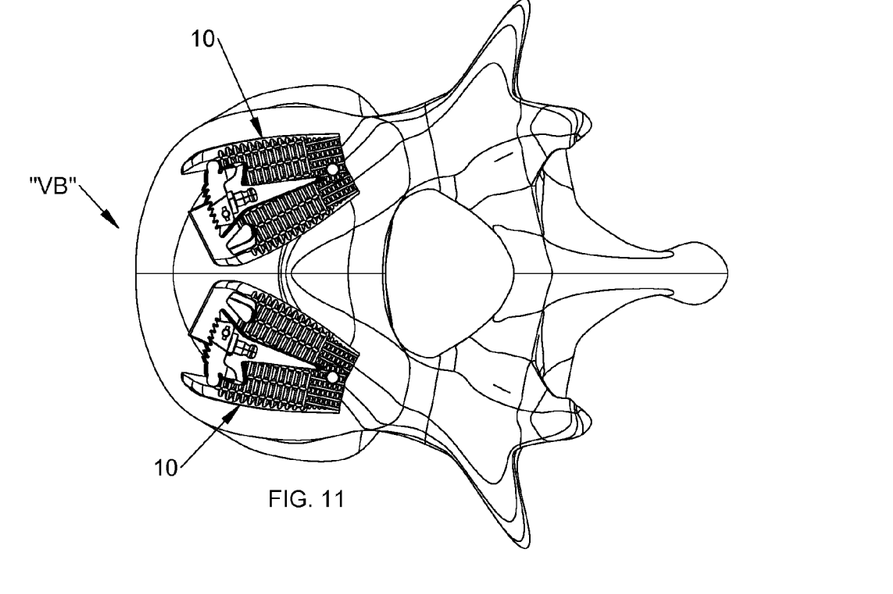
FIG. 11 is a plan view of the intervertebral space of FIG. 10, shown with two expandable spinal implants of FIG. 1 in an expanded position.

With reference to FIGS. 1-11, the insertion of an expandable spinal implant 10 into the intervertebral space during the course of a spinal surgical procedure is described. Initially, locking mechanism 400 is placed in a first, unlocked position (FIG. 8) by rotating locking mechanism in a first direction using a suitable tool (not shown) engaged with hexagonal cross section 404 of locking mechanism 400. Next, first body 100 is manipulated relative to second body 200 such that first and second bodies 100, 200 are in a first, approximated, position (FIG. 2) (e.g., closed). However, it is only necessary to perform this step if first and second body 100, 200 are not already in an approximated position. The intervertebral space is then prepared, e.g., damaged or diseased tissue is removed. Next, expandable spinal implant 10 is affixed to a suitable insertion instrument (not shown). It is contemplated that the insertion tool may also be capable of engaging the hexagonal cross section 404 of locking mechanism 400. At this point, expandable spinal implant 10 may be advanced within an incision within the patient and thereafter, into a previously prepared intervertebral space of the patient's spine (FIG. 10). The insertion instrument (not shown) is then manipulated to expand expandable spinal implant 10 in a medial-lateral direction to a desired location (FIG. 11) using the insertion instrument (not shown). Medial-lateral expansion of expandable spinal implant 10 is effectuated by manipulating first and second bodies 100, 200 about hinge pins 600, such that teeth 208, 306 cam, permitting rotation in the first direction, but not in a second, opposite direction. Expansion of expandable spinal implant adjusts the medial-lateral footprint within the intervertebral space. The desired location of first body 100 relative to second body 200 is selected based on the desired medial-lateral footprint of expandable spinal implant 10. Once a desired location has been selected, locking mechanism 400 is rotated in the second, opposite direction to lock teeth 208 of second body 200 into engagement with teeth 306 of ratchet mechanism 300 thereby locking the position of first body 100 relative to second body 200. If expandable spinal implant 10 has been expanded too far, the clinician may use a suitable tool (not shown) to retract ratchet mechanism 300 such that teeth 208, 306 become disengaged, thereby allowing expandable spinal implant 10 to rotate or pivot in the second direction and contract.

This process may be repeated as many times as the procedure requires, whether it be for the same expandable spinal implant 10 or for a plurality of expandable spinal implants 10 as required by the procedure being performed.

Expandable spinal implant 10 may be inserted using a variety of surgical techniques including, but not limited to, an anterior approach, an anteriolateral approach, a lateral approach, a retro-peritoneal approach, or a posterior approach. Expandable implant 10 is usable in a number of procedures including, but not limited to, Anterior Lumbar Interbody Fusion (ALIF), Posterior Lumbar Interbody Fusion (PLIF), and Transforaminal Lumbar Interbody Fusion (TLIF).

It will be understood that various modifications may be made to the embodiments of the presently disclosed expandable spinal implant. Therefore, the above description should not be construed as limiting, but merely as exemplifications of embodiments. Those skilled in the art will envision other modifications within the scope and spirit of the present disclosure.

What is claimed is:

1. A spinal implant, comprising:
   first and second bodies pivotably affixed to each other at respective first ends and capable of movement relative to each other, the first and second bodies dimensioned to be installed between two vertebral bodies, wherein outer surfaces of each of the first and second bodies are adapted to engage the vertebral bodies, wherein the movement of the first and second bodies is in a medial-lateral direction relative to the two vertebral bodies; and
   a ratchet mechanism pivotably supported within a slot defined in a recess of the first body, the ratchet mechanism capable of engaging a portion of the second body thereby permitting movement of the first and second bodies relative to each other in a first direction, and inhibiting movement in a second direction different than the first direction.

2. The spinal implant of claim 1, wherein outer surfaces of the first body and the second body include ridges adapted to engage the first and second vertebral bodies.

3. The spinal implant of claim 1, wherein at least one biasing element is disposed within a counterbore defined in the recess of the first body, the at least one biasing element adapted to bias the ratchet mechanism into engagement with the second body.

4. The spinal implant of claim 3, wherein the ratchet mechanism includes a first plurality of teeth disposed thereon.

5. The spinal implant of claim 4, wherein the second body includes a second plurality of teeth disposed on an interior surface thereon opposite the ratchet mechanism, the second plurality of teeth configured to engage the first plurality of teeth of the ratchet mechanism.

6. The spinal implant of claim 5, wherein the first and second pluralities of teeth are oriented such that the first and second pluralities of teeth are slidably engaged in a first direction, and are prohibited from movement relative to each other in a second direction different from the first direction, thereby defining a predetermined size of the spinal implant.

7. The spinal implant of claim 1, further including a locking mechanism disposed within an orifice defined in a side surface of the ratchet mechanism and a keyhole defined in an end face of the second body.

8. The spinal implant of claim 7, wherein the locking mechanism includes first and second ends, wherein the second end is capable of advancing axially within the keyhole in a first, unlocked position, wherein the second end is capable of locking the ratchet mechanism into a selected position when in a second, locked, position.

9. The spinal implant of claim 8, wherein the first end of the locking mechanism is attachable to a tool.

10. The spinal implant of claim 1, wherein the spinal implant is capable of being inserted between two vertebral bodies using a tool.

11. The spinal implant of claim 1, wherein the first and second bodies are capable of being manipulated relative to each other using a tool.

12. A method of performing surgery, comprising:
    providing a spinal implant comprising:
       first and second bodies pivotably affixed to each other at respective first ends and capable of movement relative to each other, the first and second bodies dimensioned to be installed between two vertebral bodies, wherein outer surfaces of each of the first and second bodies are adapted to engage the vertebral bodies; and
       a ratchet mechanism pivotably supported within a slot defined in a recess of the first body, the ratchet mechanism capable of engaging a portion of the second body thereby permitting movement of the first and second bodies relative to each other in a first direction, and inhibiting movement in a second direction different than the first direction;
    positioning the first body and the second body in a first, approximated position relative each other;
    preparing an intervertebral space between first and second vertebral bodies to receive the spinal implant;
    inserting the spinal implant into the prepared intervertebral space;
    articulating the first body and the second body relative to each other to obtain a desired medial-lateral footprint within the intervertebral space; and
    locking the ratchet mechanism to define a predetermined size of the spinal implant.

13. The method of claim 12, wherein inserting the spinal implant includes the spinal implant capable of being secured to an insertion device prior to inserting the spinal implant in the prepared intervertebral space.

14. The method of claim 12, wherein locking the ratchet mechanism includes rotating a locking mechanism disposed within an orifice defined within a side surface of the ratchet mechanism and a keyhole defined in an end face of the second body, wherein the locking mechanism includes first and second ends, wherein the second end is capable of advancing axially within the keyhole, wherein the locking mechanism is configured to be rotated to a locked position using a tool.

15. The method of claim 14, wherein locking the ratchet mechanism further includes attaching a tool to a first end of the locking mechanism.

16. The method of claim 12, wherein positioning the first body and the second body in a first, approximated, position includes engaging a first plurality of teeth disposed on a surface of the ratchet mechanism with a second plurality of teeth disposed on an opposing surface of the second body, thereby permitting articulation of the first body relative to the second body in a first direction, but not in a second direction.

17. The method of claim 12, wherein inserting the spinal implant includes the spinal implant capable of being secured to an insertion instrument.

18. The method of claim 17, wherein articulating the first body relative to the second body includes the first body and the second body configured to be articulated relative to one another using an insertion instrument.

* * * * *